United States Patent [19]

Labuda et al.

[11] Patent Number: 4,558,708
[45] Date of Patent: Dec. 17, 1985

[54] PATIENT'S AIRWAY ADAPTER TO WITHDRAW A PATIENT'S GAS SAMPLES FOR TESTING FREE OF SPUTUM MUCUS AND/OR CONDENSED WATER, BY UTILIZING A HOLLOW CYLINDRICAL HYDROPHOBIC LIQUID BAFFLE

[75] Inventors: Lawrence L. Labuda, Issaquah; Daniel W. Knodle, Seattle, both of Wash.

[73] Assignee: Tri-Med, Inc., Redmond, Wash.

[21] Appl. No.: 664,152

[22] Filed: Oct. 24, 1984

[51] Int. Cl.⁴ .............................................. A61B 5/00
[52] U.S. Cl. ................................. 128/719; 128/207.14
[58] Field of Search ................... 128/716, 719, 207.14, 128/205.23, 730

[56] References Cited

U.S. PATENT DOCUMENTS

| | | | |
|---|---|---|---|
| 3,330,271 | 7/1967 | Hozier | 128/207.14 |
| 3,544,273 | 12/1970 | McConnaughey | 128/730 |
| 3,631,654 | 1/1972 | Riely | 55/159 |
| 3,667,475 | 6/1972 | Venturelli et al. | 128/207.14 |
| 3,910,261 | 10/1975 | Ragsdale et al. | 128/719 |
| 4,090,513 | 5/1978 | Togawa | 128/207.14 |
| 4,298,358 | 11/1981 | Ruschke | 55/185 |
| 4,327,718 | 5/1982 | Cronenberg | 128/205.12 |
| 4,356,012 | 10/1982 | Hofstetter | 55/524 |
| 4,393,378 | 10/1981 | Klein | 55/528 |
| 4,406,291 | 9/1983 | Schwesinger | 128/730 |

Primary Examiner—John Doll
Assistant Examiner—A. Pal
Attorney, Agent, or Firm—Roy E. Mattern, Jr.

[57] ABSTRACT

A patient's airway adapter is fitted into a patient's airway, which is a combined breathing air supply and exhaust gas fluid flow passageway. The housing of this patient's airway adapter connects directly to a standard tapered tracheostomy or endotracheal tube connection or standard tapered portions of other fittings, and in turn provides a standard tapered connection to a patient's airway. The main air and gas stream, respectively, going to and from a patient, continues to flow directly through the patient's airway adapter. Samples of the patient's gas are withdrawn through a smaller diameter sampling exhaust port in the housing. The sampled patient's gas, immediately upon leaving the main air and gas stream, passes from the interior of a hollow cylindrical hydrophobic liquid baffle, through the baffle, and then into the sampling cannula enroute to a monitor. This hydrophobic baffle is held in a sealed position within the surrounding housing. Any mucus, sputum, and/or condensed water is kept from entering the smaller diameter sampling exhaust port, and therefore from entering the sampling cannula, as it collects on the inside of a cylindrical hydrophobic liquid baffle. The hydrophobic baffle material is a hydrophobic, hollow cylindrical baffle, having an unobstructed internal diameter in all embodiments.

19 Claims, 12 Drawing Figures

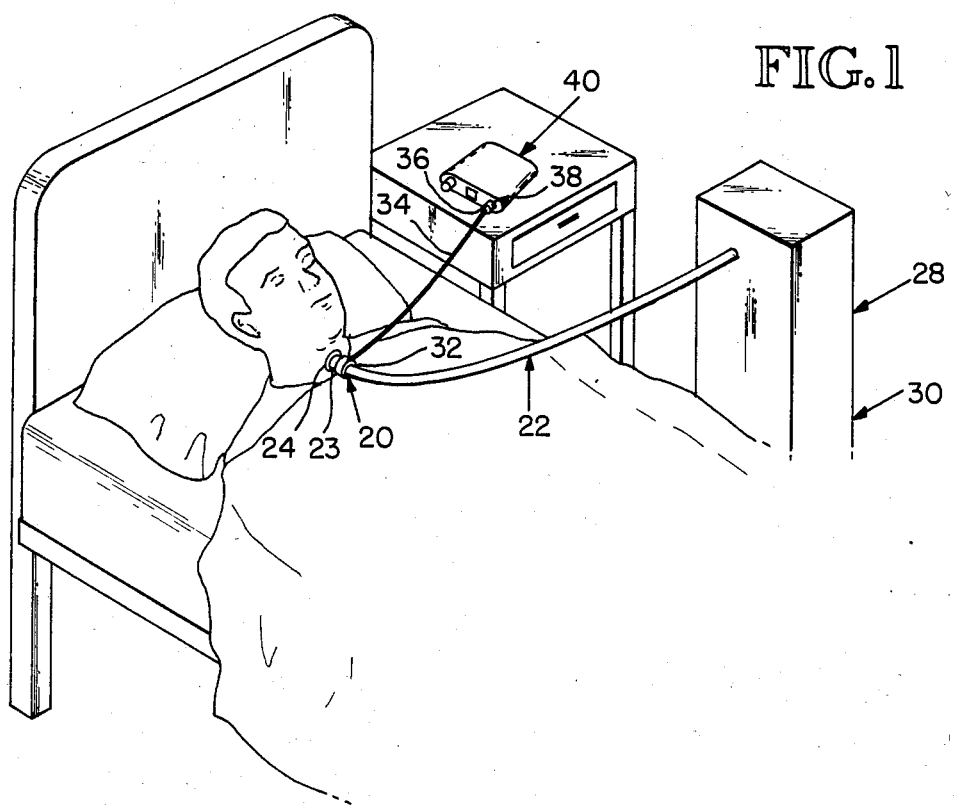
FIG. 1
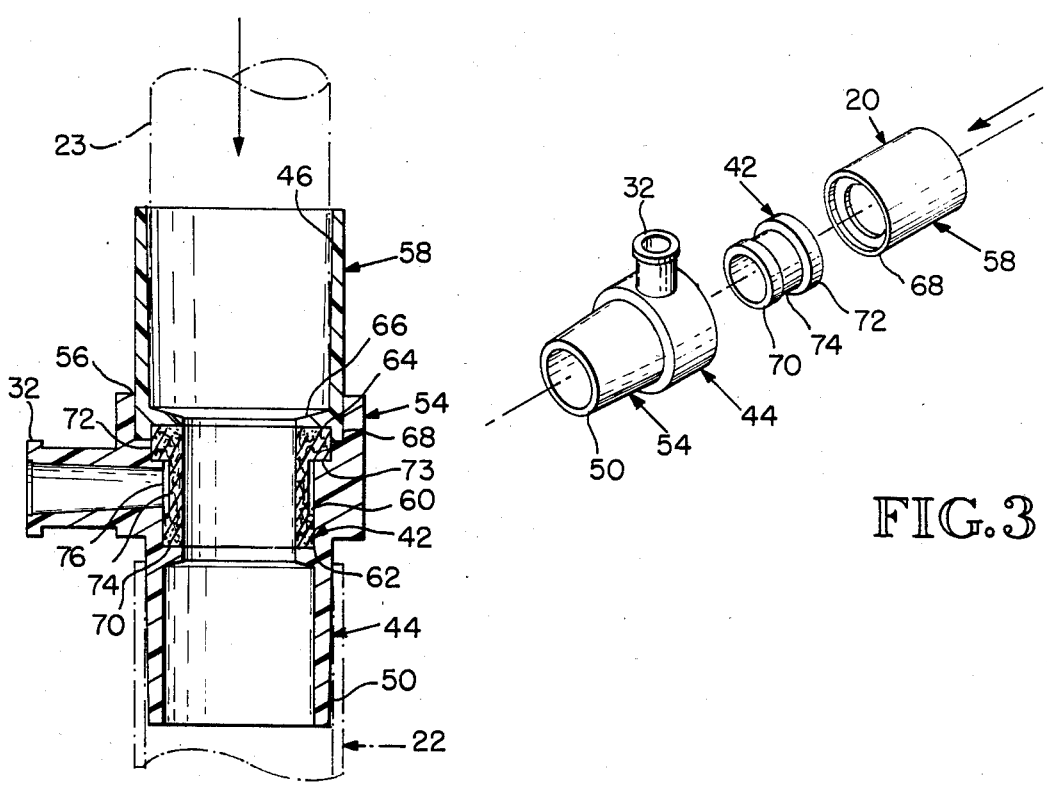
FIG. 2
FIG. 3

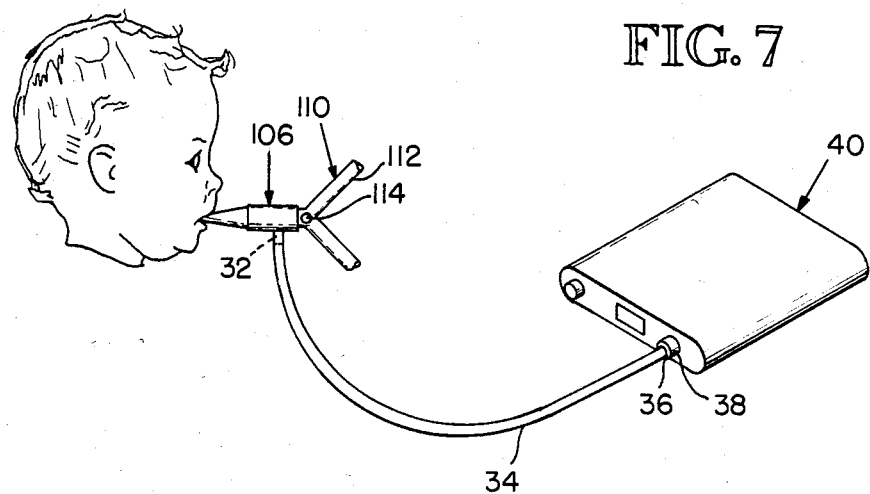
FIG. 7
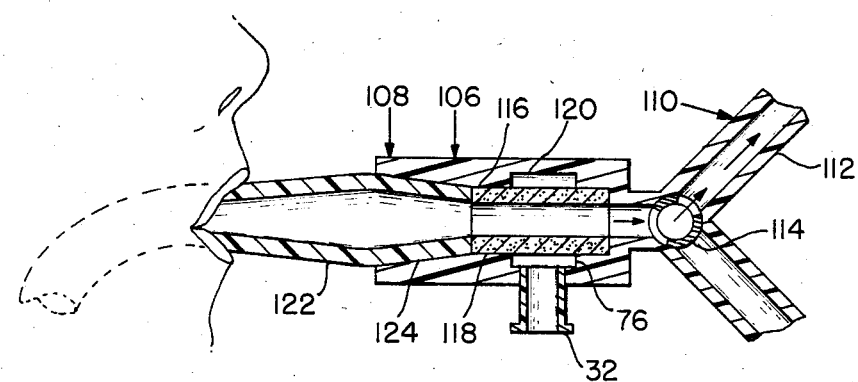
FIG. 8
FIG. 9
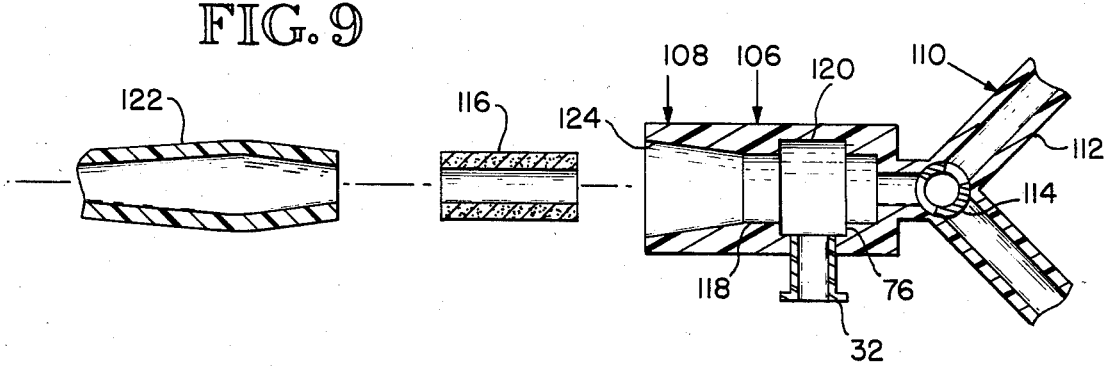

PATIENT'S AIRWAY ADAPTER TO WITHDRAW A PATIENT'S GAS SAMPLES FOR TESTING FREE OF SPUTUM MUCUS AND/OR CONDENSED WATER, BY UTILIZING A HOLLOW CYLINDRICAL HYDROPHOBIC LIQUID BAFFLE

BACKGROUND

When a patient must be aided in his or her breathing, airways, such as those of a ventilator or anesthesia circuit, are used with equipment, such as a pressure or volume regulated mechanical ventilator circuit, an anesthesia machine, or a humidified enriched gas supply circuit. When a patient is so aided, there often also is the need for placing a sampling adapter in an endotracheal or tracheostomy tube of the patient's airway, so samples of the patient's gas discharge may be taken and monitored with equipment such as a mass spectrometer, a carbon dioxide monitor, respiration or apnea monitor, or other gas analysis equipment.

Currently, commercially available sampling adapters are for example: a steel tube arranged in a right angle embodiment, with a straight portion aligned with the centerline of the airway tube, and a straight portion transversely leaving the centerline to be attached to a sampling gas cannula, which carries the sample of the patient's gas to a respective monitor; and also an adapter which has a sample port or orifice on one side of the adapter to exit a patient's gas to a cannula carrying a gas sample to a respective monitor. Both of these adapters often become clogged with either the patient's sputum, mucus, and/or condensed water. These types of adapters need protection from being blocked by liquids, while being continuously available to deliver the patient's gas samples.

Not for this purpose of keeping a patient's gas sampling line open, but for another purpose of keeping air and gas from mixing with a liquid, which is to be injected into a patient, Phyllis Riely and Robert Skyles in their U.S. Pat. No. 3,631,654 of Jan. 4, 1972, illustrate and describe their gas purge device, which incorporates a disc shaped filter in the fluid flow stream located just before the place where the stream is to be divided into a gas stream and a liquid flow. One portion of the disc is treated to become hydrophobic and another portion of the disc is left untreated and remains hydrophilic. The hydrophobic portion covers the entry to the gas stream, and the hydrophilic covers the entry to the liquid flow, establishing the desired division.

In U.S. Pat. Nos. 4,356,012 and 4,071,040, other uses of hydrophobic membranes are disclosed. Also in U.S. Pat. No. 4,327,718 a drain device is illustrated and described by Richard A. Cronenberg, which continuously removes condensate from an operational patient breathing circuit. A liquid-pervious, gas-impervious material covers a selected opening so condensate can continuously drain through the opening, while the breathing circuit is in operation.

These prior patents, known prior like equipment, and related information, indicate the use of specially treated materials to serve as membranes, baffles, and barriers, to stop gas or to stop liquid, and respectively allow the passage of liquid or gas. Also a special airway adapter was previously designed to withdraw gas from a patient's airway using a porous Teflon filter material, such as the Zitex filter material, which was formed as a large filter disc to cover the tapered entry of a small diameter sampling gas cannula. The filter disc itself was initially protected by a partial conical shield which extended partially into the airway to deflect sputum, mucus, and/or condensed water away from the filter disc located at the margin of the airway. This special airway adapter ws not made available to customers, because the design did not sufficiently overcome sealing problems, dead space problems, emptying problems, signal problems, and new air supply problems. There remained a need for an airway adapter to receive and to direct a liquid free patient's sampling gas to a sampling gas cannula and beyond to equipment monitoring the status of a patient, during relatively long periods of time, without requiring the attention of medical personnel to clean and/or to replace the sampling and testing equipment.

SUMMARY

This patient's airway adapter is used in an airway, where the patient's gas is being withdrawn into a cannula and directed to monitors, which must be protected from the entry of moisture, such as respiratory monitors, which determine the carbon dioxide level of a patient's gas, and/or such monitors which must have their sampling cannulas kept free of sputum, mucus and/or condensed water. In one embodiment this airway adapter has a non corrosive housing with both an aligned coupling entry and exit to receive standard airway tubes, having respectively an internal tracheal tube taper and an external tracheal tube taper, for example, per ANSI Z No. 79.21976. It is molded in two interfitting portions, which are insertion of an inline cylindrical hydrophobic baffle, are bonded together. In other embodiments the exit soon divides either at right angles or lesser angles, and parts or all of the airway adapter are made integrally with the airway.

The uniform diameter interior of this cylindrical hydrophobic baffle does not cause any obstruction of the passage of air and gas respectively to and from a patient by ventilation or other respiratory care procedure. In one embodiment, the variable diameter exterior of this cylindrical hydrophobic baffle provides positioning shoulder and foot portions to bear against the interior of the housing, and a circumferential recess for collecting and guiding the patient's continuous gas sample, which is passing through this hydrophobic baffle enroute to the patient's sampling gas passageway. In some embodiments the circumferential recess is provided via the housing, or via both the housing and the baffle. The patient's sampling gas passageway commences at an orientated exit port formed in the housing to receive a standard Luer fitting, for example, as specified, per ANSI No. Z70.1.1978, which is secured to the end of the cannula carrying the patient's sampling gas, for example, to a water trap and then into an apnea monitor.

The utilization of this patient's airway adapter in withdrawing a patient's gas samples for testing, free of sputum, mucus, and/or condensed water, does not add appreciably to the dead space of an airway, and does permit long term respiratory gas sampling, while maintaining normal airway patency and pressures. After extended periods of gas sampling the hydrophobic baffle becomes saturated, the entire airway adapter is disposed of, and a new one is installed, or if it is integrally included, in part or in whole, entire portions of an airway may be disposed of.

DRAWINGS

Preferred embodiments of patient's airway adapters to withdraw gas samples for testing and how they are used are illustrated in the drawings, wherein:

FIG. 1 is a perspective view of a patient having a tracheostomy airway being assisted in his or her breathing via the operation of ventilator circuit equipment, wherein the patient's airway adapter in one embodiment is installed to direct the patient's gas sample, for example, after passing through a baffle, to a carbon dioxide respiration monitor;

FIG. 2 is an enlarged cross sectional view, in reference to FIG. 1, taken through a portion of the anesthesia circuit, shown with dotted lines, where the patient's airway adapter is installed with arrows indicating the gas flow, as the patient is exhaling, and a first embodiment of a baffle of the patient's airway adapter is shown;

FIG. 3 is an exploded view, in reference to FIG. 2, with some portions removed, to illustrate the components of this embodiment of the patient's airway adapter before they are assembled, and the first embodiment of the baffle is shown, having a recessed portion to form a ring like collecting volume of the patient's gas, before it enters the sampling cannula;

Figure 4:
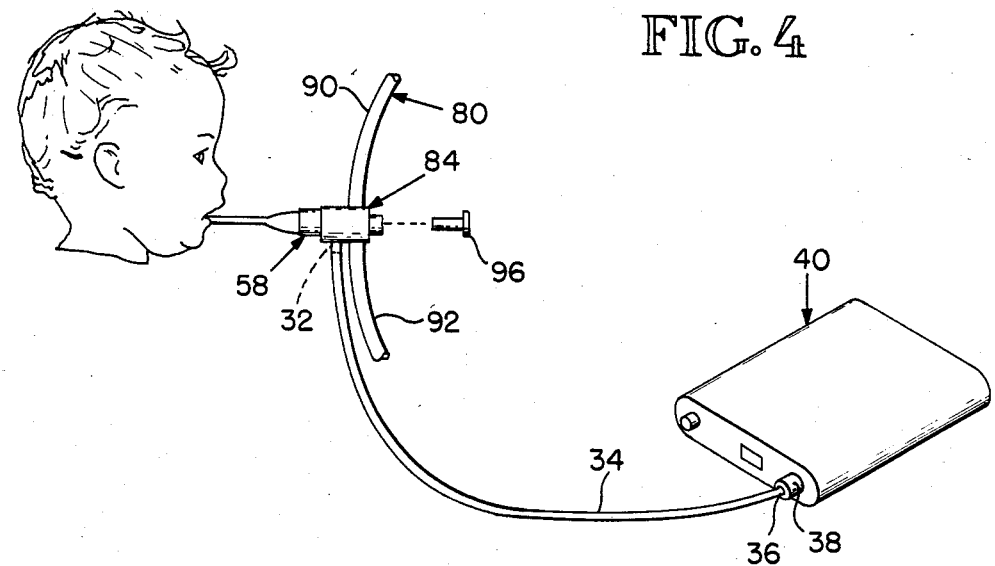
Figure 5:
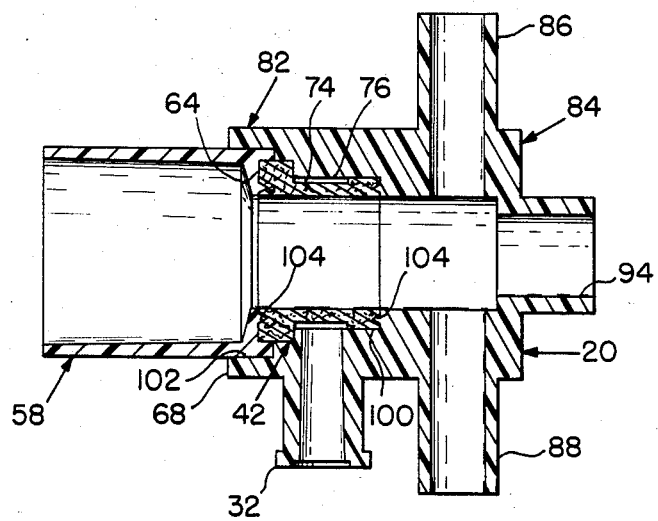
Figure 6:
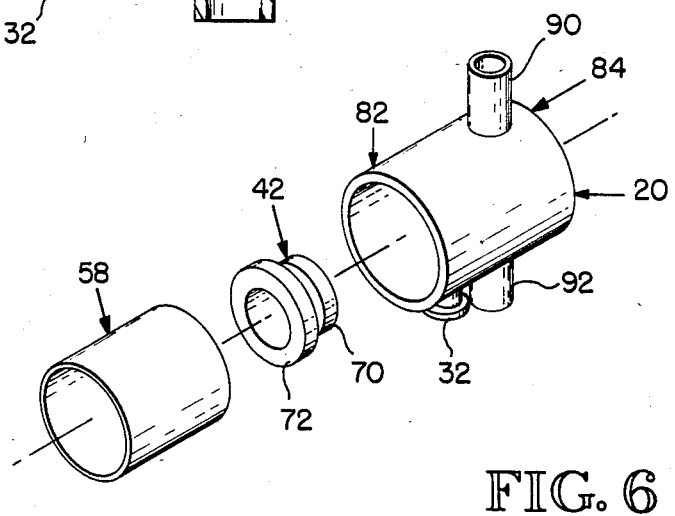

FIG. 4 is a perspective, partial and somewhat schematic view of a patient having an endotracheal airway, being assisted in breathing, via operation of equipment, not shown, which utilizes dual airways going to and from this equipment, and therefore the patient's airway adapter in this second embodiment is installed not only to direct the patient's gas sample, for example, to a carbon dioxide respiration monitor, but also to guide the gas flows to and from the respective dual airways;

FIG. 5 is a sectional view of this second embodiment of the patient's airway adapter as shown in FIG. 4 with a first embodiment of a baffle;

FIG. 6 is an exploded view, in reference to FIGS. 4 and 5, with some portions removed, to illustrate the components of this second embodiment of the patient's airway adapter, having the first embodiment of a baffle;

FIG. 7 is a perspective, partial, and somewhat schematic view of a patient having an endotracheal airway, being assisted in breathing, via operation of equipment, not shown, which utilizes dual airways going to and from this equipment, and therefore the patient's airway adapter in this third embodiment is installed not only to direct the patient's gas sample, for example, to a carbon dioxide apnea monitor, but also to guide the gas flows to and from the respective dual airways, and portions of the airway adapter are made integrally with an airway component, and also a second embodiment of a baffle of the patient's airway adapter is shown;

FIG. 8 is a cross sectional view indicating how this third embodiment of the patient's airway adapter is made integrally in part with the airway equipment, and how it receives a patient's endotracheal tube.

Figure 10:
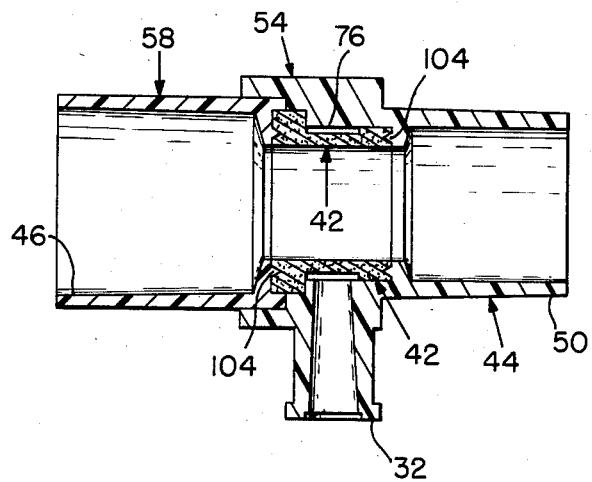
Figure 11:
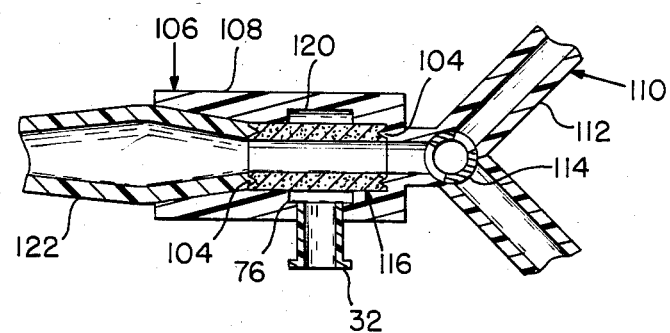
Figure 12:
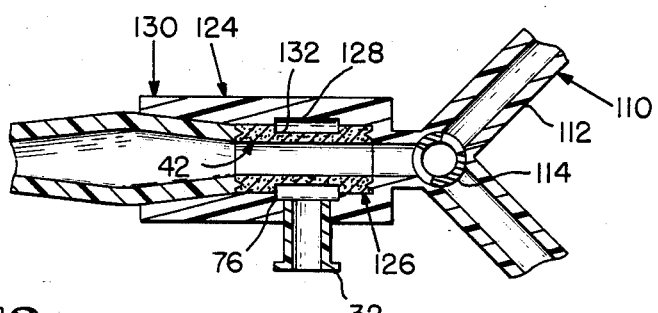

FIG. 9 is an exploded view of the third embodiment of the patient's airway adapter;

FIG. 10 is a partial section of the first embodiment of the patient's airway adapter and the first embodiment of the baffle, indicating how the housing is formed with sealing tips, to create respective seals to prevent wicking, which might otherwise occur, decreasing the effectiveness of the baffle, and therefore decreasing the effectiveness of the patient's airway adapter;

FIG. 11 is a partial section of the third embodiment of the patient's airway adapter, and the second embodiment of the baffle, indicating how the housing is formed with sealing tips, to create respective seals to prevent wicking, and how the housing is formd to provide the ring like collecting volume of the patient's gas, before it enters the sampling cannula; and FIG. 12 is a partial section, somewhat like FIG. 11, showing, however, a fourth embodiment of a patient's airway adapter, and a third embodiment of the baffle, also indicating how the housing is formed with sealing tips, but moreover indicating how both the housing and the baffle are complementary contoured to provide the circumferential ring like volume of the sampled patient's gas, which has passed through the baffle and then is collected for distribution into the patient's gas sampling cannula.

DESCRIPTION OF PREFERRED EMBODIMENTS

Introduction

The patient's airway adapter 20 in its several embodiments is utilized to withdraw a patient's gas samples for testing, free of sputum, mucus, and/or condensed water. During some of the many respiratory care procedures that are undertaken today, and at other times, the personnel caring for a patient want to constantly know if their patient is breathing sufficiently. Preferably to detect all forms of apnea, known as central, mixed, and obstructive, a monitor must accurately respond to pulmonary gas exchange instead of just the patient's ventilatory effort. Monitoring or detecting the adequate continuous range of exhaled carbon dioxide in a patient's gas is recognized as being a reliable method of fully monitoring a patient's breathing. However, a respiration monitor of the patient's exhaled carbon dioxide must be reliably protected from moisture, and a gas sampling cannula must be kept clear for extensive patient care periods. Extensive operating time periods of monitoring equipment, are especially needed during the night, when fewer nurses are on duty to assist patients.

A General Arrangement

Therefore, for example, as illustrated in FIG. 1, this patient's airway adapter 20 is installed in the patient's airway 22, generally near where the airway 22 commences near the patient's face or throat, commencing, for example, at a tracheostomy fitting 24, endotracheal tube, not shown, or other fitting, secured to the patient, and in turn secured to the standard patient's airway fitting 23. The patient's airway 22 then extends from this patient's airway adapter 20, for example, on to a ventilator 28, which is providing a source of medical gas for the overall respiratory therapy equipment 30.

From an opening 32, which may be a standard Luer fitting 32, on the side of the patient's airway adapter 20, the patient's gas sampling cannula 34 extends to an opening 36, which may be a standard Luer fitting 36, on a water trap 38, which in turn is fitted to a respiration monitor 40. The water trap 38 is the last line of moisture defense in protecting the respiration monitor 40. Therefore to prolong the water trap's life, to initially eliminate all condensed water, and to stop sputum and/or mucus from entering the patient's gas sampling cannula 34, the patient's airway adapter 20, is equipped with an effective hydrophobic baffle 42, as shown in FIGS. 2 and 3, without hindering flow in the patient's airway 22, and without hindering flow in the patient's gas sampling cannula 34, during very extended operating time periods.

Patient's Airway Adapter—Housing

The patient's airway adapter 20, in respect to one embodiment, which conveniently and accurately positions the effective hydrophobic baffle 42, in a centered flow through interior receiving chamber 60, is illustrated in the cross sectional view of FIG. 2 and in the exploded view of FIG. 3. A two piece housing 44 positions and holds the hydrophobic baffle 42 in place and provides: the patient's airway fitting taper receiver 46 for the patient's airway fitting 23 secured to the patient's tracheostomy fitting 24; the patient's airway taper receiver 50 for the airway 22 going to the ventilator 28; and the connector 32 f the patient's gas sampling cannula 34.

Preferably one piece, referred to as the baffle receiving piece 54 of the housing 42, is formed in a molding process to include the centered flow through patient's airway taper receiver 50, the transverse radially positioned connector 32, a top circular shouldered entry 56 to receive the other piece, referred to as the baffle securing piece 58, and a centered flow through interior receiving chamber 60, to receive and to position the hydrophobic baffle 42. To specifically position the hydrophobic baffle 42, this receiving chamber 60 is formed to include a lower or foot receiving internal circular abutment 62, and a top or shoulder receiving internal circular abutment 64, which is axially adjacent to the top circular shouldered entry 56.

The other piece, referred to as the baffle securing piece 58, of the two piece housing 44, has at its top the centered flow through internal patient's airway fitting taper receiver 46. Near its bottom is a circular retaining shoulder 66, which contacts the top of the hydrophobic baffle 42. Beyond this circular retaining shoulder 66, this baffle securing piece 58 is continued as a circular rim 68 to center it about the top of the hydrophobic baffle 42, and to fit inside the top circular shouldered entry 56 of the baffle receiving piece 54.

Both these pieces of housing 44, are preferably molded using a resulting non corrosive material. After the placement of the hydrophobic baffle 42 in the receiving chamber 60 of the baffle receiving piece 44, and the axial insertion of baffle securing piece 58 over the end of the hydrophobic baffle 42 and partially into the baffle receiving piece 54, these two pieces 54, 58 of the housing 44 are bonded together throughout their interfitting portions, as shown in FIGS. 2 and 3.

Patient's Airway Adapter—Hydrophobic Baffle

The hydrophobic baffle 42, which is firmly and sealably positioned in the two piece housing 44 of the patient's airway adapter 20, is preferably molded using a high density polymer material of preferably a small pore size, selected from a range of five to thirty micron pore sizes. To functionally interfit and perform within the two piece housing 44, this hydrophobic baffle 42 has a foot portion 70, serving as its entry portion during assembly and also serving to abut the lower or foot internal circular abutment 62 of the receiving chamber 60 of the baffle receiving piece 54. It also has a top shoulder portion 72 serving to contact and to rest upon the top or shoulder receiving internal circular abutment 73 of the receiving chamber 60 of the baffle receiving piece 54.

Between this top shoulder portion 72 and the foot portion 70, the hydrophobic baffle 42 has a circumferential recessed portion 74, which after installation, forms a cylindrical ring collecting chamber 76 in conjunction with the receiving chamber 60 of the interior of baffle receiving piece 54 of the two piece housing 44. In this chamber 76 the patient's sampling gas, after passing through the hydrophobic baffle 42, collects as an ample supply, before being guided into the patient's continuous gas sampling cannula 34 or passageway.

As illustrated in FIGS. 2 and 3, the outer surfaces throughout the hydrophobic baffle 42, and surfaces of the volume of the cylindrical ring collecting chamber 76, are proportionally larger than the cross sectional area of the patient's gas sampling cannula 34. As an intended consequence, the patient's carbon dioxide gas monitoring times or other monitoring times, are very practically extended for convenient patient respiratory care periods. These comparatively large surface areas of the hydrophobic baffle 42 allow the continuous sampling of the patient's gas to take place, via this gas flowing through the hydrophobic baffle 42, even if one half or more of its surface, exposed to the patient's airway 22, is blocked off by the barrier effect of the contaminants, such as sputum, mucus, and/or condensed water.

Preferably the patient's airway adapter 20 will operationally outlast any patient's respiratory testing care period, or it will be promptly changed upon a blockage signal emitted from a monitor, such as an apnea monitor 40. However, even if the barrier becomes completely blocked, some contaminants soon will be pulled through the hydrophobic baffle 42, in sufficient portions of small enough sizes, so the patient's sampling gas passageway will be operationally formed again. Thereafter, the hydrophobicity of the baffle 42, continues on in its function to prevent any long term blockage of the patient's gas sampling cannula 34 by any contaminants.

Another Embodiment Wherein the Housing of the Patient's Airway Adapter Also Serves as a Tee Connector When the patient being monitored is an infant, the infant's overall airway circuit 80 should have the least dead space as possible. Therefore, a housing 82 of another embodiment 84 of the patient's airway adapter 20 is arranged to include tee connector portions 86, 88, which are arranged perpendicular to the central axis of a like hydrophobic baffle 42, as illustrated in FIGS. 4, 5, and 6. These tee portions 86, 88, are connected to branches 90, 92 of the infant's airway circuit 80. The in line opening 94 may be used for access during cleaning and insertion of catheters, not shown, and thereafter fitted with a sealing member 96. The housing 82 has an internal central cylindrical space 100 to receive the hydrophobic baffle 42, and an adjacent internal central cylindrical space 102 to receive the baffle securing piece 58 at the circular rim 68. The circular retaining shoulder 64 of the baffle securing piece 58 has a circular projecting seal tip 104, which slightly penetrates into the hydrophobic baffle 42, and serves to prevent wicking. At the other end of the hydrophobic baffle 42, housing 82 has a like formed circular projecting sealing tip 104, for the same purpose of preventing wicking.

The exploded view of FIG. 6 illustrates how these three components, i.e. the housing 82, the hydrophobic baffle 42, and the baffle securing piece 58, may be quickly assembled to form this embodiment 84, creating an airway adapter 20, especially useful for an infant's airway circuit 80. The essential portions of the first illustrated embodiment of the patient's airway adapter 20, and the essential portions of a tee fitting are combined in this second embodiment 84.

Another Embodiment, Wherein the Housing of the Airway Adapter is Molded as an Integral Part or Portion of a Disposable Airway Circuit In FIGS. 7, 8, and 9, another embodiment 106 is illustrated, wherein the housing 108 is molded as an integral portion of a disposable airway circuit 110. This circuit 110 could be of any selected configuration; however it is shown commencing with a Y portion 112, which positions an exhalation valve 114, which alternately controls the direction of the gas flow in the patient's disposable airway circuit 110.

A second embodiment 116 of a hydrophobic baffle 116 is shown. It is essentially a hollow cylinder 116 of uniform thickness. The interior central cylindrical space 118 of the housing 108, which receives this hydrophobic baffle 116, is formed with an internal or interior cylindrical recess 120, which completely serves as the cylindrical collecting chamber 76 positioned about the hydrophobic baffle 116. The standard Luer fitting 32 is fitted to the housing 108 to serve as the exit from the cylindrical collecting chamber 76 and to connect to the patient's gas sampling cannula 34.

A patient's endotracheal tube 122 is fitted into a tapered interior central space 124 of the housing 108 of this embodiment 106 of a patient's airway adapter 20. Different selectable sizes of endotracheal tubes 122 are available to fit the patient, i.e. a baby, a child, or an adult.

Features of All Embodiments and Other Embodiments

In FIG. 10, portions of the first embodiment of the patient's airway adapter 20 are illustrated to indicate the addition of sealing tips 104 to both the baffle securing piece 58 and the baffle receiving piece 54 of the two piece housing 44, which receives and positions the hydrophobic baffle 42. The utilization of these sealing tips 104 prevents wicking of moisture past the ends of hydrophobic baffle 42.

In FIG. 11, the third embodiment 106 of the patient's airway adapter 20, and the second embodiment 116 of the hydrophobic baffle 42 are shown to indicate how the housing is formed with sealing tips 104 to create the respective seals which prevent wicking. Also illustrated is the ring like collecting chamber 76 for the patient's gas, before it enters the sampling cannula 34. This collecting chamber 76 is formed in the housing 108 via the internal or interior cylindrical recess 120.

In FIG. 12 a fourth embodiment 124 of the patient's airway adapter 20 and a third embodiment 126 of the hydrophobic baffle 42 are illustrated, to indicate how the cylindrical ring collecting chamber 76 is created, by forming an interior cylindrical recess 128 in the housing 130, and by forming an opposite exterior cylindrical recess 132 in the third embodiment 126 of the hydrophobic baffle 42.

Specific References to Selected Materials, Processes and Sizes Used in Reference to All Embodiments A large portion of the currently used airways use standard tapers based on fifteen millimeter diameter patient's airway passageways. A selected hydrophobic baffle material is a hydrophobic, fifteen micron sized high density polyethylene formed into the respective hollow cylindrical baffles. Preferably these hydrophobic baffles are molded gaining smooth surfaces. If they are to be machined in part or throughout, then the machine surfaces are melted to gain the smooth surfaces required for these hydrophobic baffles. If the machine cuts are left exposed, the baffles are less hydrophobic.

Housings of the various embodiments are made from non corrosive materials, such as from a high impact polystyrene material. General size specifications are often based on standards designated as ANSI No. Z79.2-1976.

The overall purpose in making and using these patient's airway adapters is to extend the monitor operating times as long as possible, keeping the mucus, sputum and/or condensed water from entering the patient's gas sampling cannula.

We claim:

1. A patient's airway adapter to withdraw a patient's gas samples from a patient's airway for testing in a respiratory monitor, free of sputum, mucus, and/or condensed water, comprising:
    (a) a housing having:
        an interior to continue the patient's airway passageways extending between a patient and respiratory sustaining equipment;
        a centered flow through interior receiving chamber within the interior of the housing to receive a hydrophobic membrane type liquid blocking but gas passing baffle;
        a passageway extending essentially radially outwardly through the housing from the centered flow through interior receiving chamber;
        a connector portion on this passageway extending through the housing, to receive a patient's gas sampling cannula;
        respective connector portions on the housing adapted to interfit with endotracheal or tracheal tubes or other airway components extending to a patient;
        respective connector portions on the housing adapted to interfit with tubes or other airway components extending to respiratory sustaining equipment; and
    (b) a hollow cylindrical hydrophobic membrane type baffle received in the centered flow through interior receiving chamber within the interior of the housing: to continue the interior of the patient's airway passageway; to block the radial passage of sputum, mucus, and/or water; and to allow the radial passage of the patient's gas through this hollow cylindrical hydrophobic membrane type baffle, through the radial passageway of the housing and beyond through a patient's gas sampling cannula to a respiratory monitor.

2. A patient's airway adapter, as claimed in claim 1, wherein the housing is made of two pieces, one piece, serving as a baffle receiving piece, has:
    a centered flow through externally tapered receiver serving as a respective connector portion adapted to interfit with endotracheal or tracheal tubes or other airway components;
    a transverse radially positioned standard Luer connector serving as the connector portion to receive a patient's gas sampling cannula;
    a top circular shouldered entry to receive the other piece designated as a baffle securing piece; and
    the centered flow through interior receiving chamber, having in turn:
        a foot receiving internal circular abutment; and a shoulder receiving internal, circular abutment, which is axially adjacent to the top circular shouldered entry;

whereby the abutments both serve to receive the hollow cylindrical hydrophobic membrane type baffle.

3. A patient's airway adapter, as claimed in claim 2, wherein the other piece of the housing, serving as a baffle securing piece, has:

a top centered flow through internally tapered receiver, serving as a respective connector portion adapted to interfit with tubes or other airway components extending to respiratory sustaining equipment;

a circular retaining shoulder near its bottom to bear against the hollow cylindrical hydrophobic membrane type baffle; and a circular rim to fit inside the top circular shouldered entry of the baffle receiving piece.

4. A patient's airway adapter, as claimed in claim 3, wherein the hollow cylindrical hydrophobic membrane type baffle has:

a foot portion to abut the foot receiving internal circular abutment of the baffle receiving piece of the two piece housing;

a top shoulder portion to contact and to rest upon the shoulder receiving internal circular abutment of the baffle receiving piece; and a circumferential recessed exterior portion located between this foot portion and this top shoulder portion; which after installation of this baffle in this baffle receiving piece, forms a cylindrical ring collecting chamber in conjunction with the interior of this baffle receiving piece, whereby the patient's gas, essentially free of moisture, is collected in ample quantity to supply the radial flow of the patient's gas through the patient's gas sampling cannula to a respiratory monitor.

5. A patient's airway adapter, as claimed in claim 4, wherein, after the placement of the hollow cylindrical hydrophobic membrane type baffle into the baffle receiving piece of the housing and the subsequent interfitting of the baffle securing piece of the housing against this baffle and partially within the baffle receiving piece of the housing, then these two pieces of the housing are bonded together.

6. A patient's airway adapter, as claimed in claim 5, wherein the two piece housing is molded using high impact polystyrene material.

7. A patient's airway adapter, as claimed in claim 6, wherein the hollow cylindrical hydrophobic membrane type baffle is molded using a high density polyethylene material.

8. A patient's airway adapter, as claimed in claim 7, wherein the high density polyethylene material has micron pore sizes selected in a range of five to thirty micron pore sizes.

9. A patient's airway adapter, as claimed in claim 7, wherein the high density polyethylene material has a fifteen micron pore size.

10. A patient's airway adapter, as claimed in claim 1, wherein the exterior of the hollow cylindrical hydrophobic membrane type baffle and the centered flow through interior receiving chamber within the interior of the housing are complementary formed to create a collecting chamber for the patient's gas in an ample quantity to keep the patient's gas sampling cannula full during a respiratory monitoring period.

11. A patient's airway adapter, as claimed in claim 1, wherein the hollow cylindrical hydrophobic membrane type baffle has an exterior circumferential recessed portion, which together with the centered flow through interior receiving chamber within the interior of the housing, forms a collecting chamber for the patient's gas in an ample quantity to keep the patient's gas sampling cannula full during a respiratory monitoring period.

12. A patient's airway adapter, as claimed in claim 1, wherein the hollow cylindrical hydrophobic membrane type baffle has an exterior circumferential recessed portion, and the centered flow through interior of the housing has an interior circumferential recessed portion, and these circumferential recessed portions together form this collecting chamber of the patient's gas in an ample quantity to keep the patient's gas sampling cannula fall during a respiratory monitor period.

13. A patient's airway adapter as claimed in claim 1 comprising in addition integral portions of the patient's airway circuit, thereby making the patient's airway adapter housing an integral part of the patient's airway circuit.

14. A patient's airway adapter, as claimed in claim 1, comprising in addition integral portions of a tee connection used in the patient's airway circuit, thereby making the housing of the patient's airway adapter an integral part of this tee connection.

15. A patient's airway adapter, as claimed in claim 1, comprising in addition integral portions of a Y connection used in the patient's airway circuit, thereby making the housing of the patient's airway adapter an integral part of this Y connection.

16. A hollow cylindrical hydrophobic membrane type baffle to continue the interior passageways of tubes of a patient's airway and to block the radial passage of sputum, mucus, and/or water, while allowing the radial passage of a patient's gas sampling cannula to a respirator monitor.

17. A hollow cylindrical hydrophobic membrane type baffle, as claimed in claim 16, wherein an outer circumferential recessed portion is formed in the baffle to create a collecting volume for an ample quantity of a patient's gas to keep a patient's gas sampling cannula full during a respirator monitoring period.

18. A hollow cylindrical hydrophobic membrane type baffle, as claimed in claim 16, wherein a high density polyethylene material is used as the baffle material in a range of five to thirty micron pore sizes, with a fifteen micron pore size being preferred.

19. A hollow cylindrical hydrophobic membrane type baffle, as claimed in claim 17, wherein a high density polyethylene material is used as the baffle material in a range of five to thirty micron pore sizes, with a fifteen micron pore size being preferred.

* * * * *